United States Patent [19]
Lacey

[11] Patent Number: 5,379,630
[45] Date of Patent: Jan. 10, 1995

[54] THERMAL CONDUCTIVITY DETECTOR

[75] Inventor: Richard F. Lacey, Palo Alto, Calif.

[73] Assignee: Hewlett-Packard Company, Palo Alto, Calif.

[21] Appl. No.: 84,652

[22] Filed: Jun. 28, 1993

[51] Int. Cl.$^6$ .......................................... G01N 25/18
[52] U.S. Cl. ................... 73/25.03; 73/202.5; 73/204.15; 73/35; 422/96; 324/105; 324/450
[58] Field of Search ................ 73/25.03, 35.05, 202.5, 73/204.11, 204.15; 324/105, 62; 422/96

[56] References Cited

U.S. PATENT DOCUMENTS

| | | | |
|---|---|---|---|
| 3,449,951 | 6/1969 | Westersten | 73/861.11 |
| 3,683,671 | 8/1972 | Van Swaay | 73/25.03 |
| 3,733,545 | 5/1973 | Elsner et al. | 324/520 |
| 3,864,959 | 2/1975 | MacDonald | 73/25.03 |
| 4,496,900 | 1/1985 | Di Stefano et al. | 324/71.1 |
| 4,649,745 | 3/1987 | Kondo et al. | 73/118.2 |
| 4,735,082 | 5/1988 | Kolloff | 73/25.03 |
| 4,850,714 | 7/1989 | Wiegleb | 73/25.03 |
| 4,872,339 | 10/1989 | Gerhard et al. | 73/118.2 |
| 4,918,974 | 4/1990 | Hachey et al. | 73/25.03 |
| 5,233,308 | 8/1993 | Willis | 73/25.03 |

OTHER PUBLICATIONS

Dr. Dietrich Jentzsch and Dipl-Ing. Eginhard Otte, "Detectors in Gas Chromatography: Wheatstone Bridge for AC Operation", Academic Publishing Co, Frankfurt, Germany, 1970, pp. 121-122 and pp. 154-157.

Primary Examiner—Thomas P. Noland
Assistant Examiner—David Wiggins

[57] ABSTRACT

In one embodiment, a thermal conductivity detector in a gas chromatograph is provided with a sensor connected in a resistive bridge with an alternating voltage applied to the bridge. Changes in thermal conductivity of a gas in the sensor cause changes in the temperature and resistance of the sensor which unbalances the bridge. A component of the voltage difference caused by the imbalance varies as the third harmonic of the applied voltage and has a magnitude related to the thermal conductivity of the gas. This third harmonic is measured to determine the thermal conductivity of the gas. In another embodiment, a sensor in a cavity through which gas flows is alternately operated at two different temperatures, and a difference in power required for operation is measured. The difference is independent of the temperature of the cavity walls and proportional to the thermal conductivity. This difference is measured to determine the thermal conductivity of the gas.

14 Claims, 2 Drawing Sheets

THERMAL CONDUCTIVITY DETECTOR

BACKGROUND OF THE INVENTION

1. Field of the Invention

This invention relates to thermal conductivity measurement devices, and in particular, to precision measurement devices for measuring the thermal conductivity of a fluid, such as a gas, to detect compounds within the fluid.

2. Description of Related Art

Gas chromatographs are used to determine the chemical composition of a sample, which may be gaseous or a vaporized liquid. The term gas will hereinafter be used to include a vapor. In one type of gas chromatograph, a sample is sent through a separation column. A typical separation column is a long capillary tube with a coated interior. Different chemical compounds in the sample travel through the separation column at different rates and leave the separation column at different times. As compounds leave the separation column, they are carried by a carrier gas past a detector. One commonly used carrier is helium, but other gases may be used. The detector detects compounds in the carrier gas by measuring changes in the properties of the effluent gas. When a change in the gas property occurs, the timing of the change indicates the type of the compound passing the detector, and the magnitude of the change indicates the quantity of the compound.

One type of detector used with gas chromatographs is a thermal conductivity detector, which detects changes in the thermal conductivity of the effluent gas. When a compound is mixed with the carrier gas, the thermal conductivity of the mixture is usually different from that of the pure carrier gas. A thermal conductivity detector provides a measure of the change in the thermal conductivity of the carrier gas and thereby provides a measure of the presence and amount of various compounds.

FIG. 1 shows a typical prior art sensor circuit 10 used in a thermal conductivity detector of a gas chromatograph. The sensor circuit 10 includes a metal filament 12, such as a platinum wire, placed in a cavity 14. The effluent from a gas separation column along with a carrier gas fills the cavity 14 and flows along a path 16 past the filament 12. The filament 12 has a resistance $R_S$ which depends on its temperature and is heated using an electric current $I_1$. In the case of the filament 12 being a platinum wire, the resistance of the filament 12 is proportional to its temperature.

Heat generated by the filament 12 is removed partially by the flow of the effluent but primarily by thermal conduction through the gas to the walls 18 of the cavity 14, thus lowering the resistance of the filament 12. By effectively measuring the change in resistance of the heated filament 12, the change in thermal conductivity of the flowing gas may be determined.

In application, several problems arise that can cause the output of a detector to change even if the composition of the gas remains constant. One problem is caused by changes in the temperature of the walls 18 of the cavity 14. Another problem is caused by changes in the temperature of the carrier gas. Another problem is electronic drift of the energizing voltage which controls the current through the filament 12. With the sensitivity required of a detector, even thermoelectric potentials generated in electrical connections may affect the detector. Changes in the voltage offset of the amplifiers used to measure changes in the resistance of filament 12 are still another problem.

One technique for trying to avoid some of these problems is using the filament 12 in a bridge circuit employing a control filament 22 (FIG. 1) which is ideally identical to the filament 12 and is located in a cavity 24 similar to the cavity 14 but containing only a pure carrier gas. A variable resistor $R_b$ is used to match the resistance of a fixed resistor $R_a$. A differential amplifier 26 detects an unbalance in the bridge. A DC voltage supply is used to heat up the filaments 12 and 22 to a temperature typically between 5° to 100° C. above the temperature of the cavity walls 18.

If the thermal conductivity of the effluent in the cavity 14 is different from that of the pure carrier gas in cavity 24, the bridge becomes unbalanced, and a change in the amplifier's output voltage $V_A$ indicates the detection of a change in thermal conductivity of the gas in the cavity 14. Common variations in the wall temperature of the cavities 14 and 24 as well as common variations in the temperature of the carrier gas change the resistances of the filaments 12 and 22 equally and do not affect $V_A$. Similarly, a fluctuation in $V_{DC}$ does not affect $V_A$ if the cavities 14 and 24 and filaments 12 and 22 are identical.

A problem with this method is that two different sensors cannot be made exactly the same and would, therefore, not react identically to identical changes in their ambient environment. And, even if the sensors could be made to be initially identical, the properties of the sensors change with time, producing a bridge imbalance with common changes in the ambient environment of the filaments 12 and 22.

Accordingly, improved methods and structures for detecting thermal conductivity are needed to avoid the detrimental effects due to imprecise matching of the sensor resistor in a bridge type sensor circuit.

SUMMARY OF THE INVENTION

In one embodiment of the invention, a sensor filament resistor, located inside a sensor cavity through which the effluent of a gas chromatograph flows, is connected to fixed resistors in a bridge arrangement, and a sinusoidally alternating voltage is applied to the bridge. The frequency of the applied voltage is low enough so that the temperature of the sensor substantially tracks the instantaneous power provided to the sensor, and its resistance changes accordingly. The nonlinearity of resistance with current generates a voltage component across the sensor resistor that is at the third harmonic of the applied alternating voltage. A change in the thermal conductivity of a gas, or other fluid, flowing across the sensor changes the temperature and resistance of the sensor and changes the voltage output of the bridge. The change in the third harmonic component of the output voltage across the bridge has a magnitude that depends on the change in thermal conductivity of the gas. This change in third harmonic is measured and provides a signal which is virtually independent of electronic offsets and drifts which are unrelated to the third harmonic of the frequency of the energizing voltage.

In a second preferred embodiment of the invention, a compensation resistor within a separate cavity is connected along with the sensor resistor in a bridge arrangement to reduce changes in the third harmonic component of the bridge voltage generated by common mode temperature variations of the walls of the sensor and compensator cavities and by variations in the amplitude of the exciting sinusoidal voltage. Effects of these common mode variations cannot be completely eliminated, however, because the sensor and compensating cells are not completely identical.

In another embodiment of the invention, a thermal conductivity sensor resistor is alternately operated at two different temperatures, and the power required for heating the sensor resistor to the two temperatures is measured. The difference between the power measurements provides a signal that is independent of the ambient temperature of the cavity.

DETAILED DESCRIPTION OF THE PREFERRED EMBODIMENTS

The present invention provides methods and structures for measuring thermal conductivity in a manner that is independent of electronic and ambient temperature drift.

Figure 2:
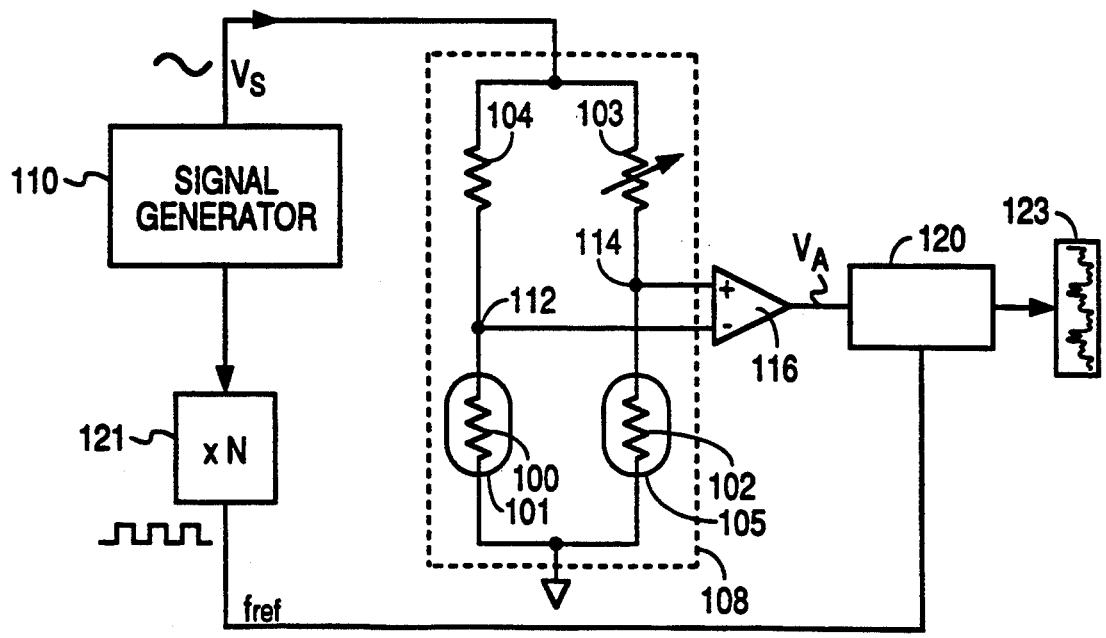
FIG. 2 is a schematic diagram of a thermal conductivity detector that measures the third harmonic of a voltage across a bridge.

FIG. 2 is a schematic diagram of a thermal conductivity detector, in accordance with the invention, that measures the third harmonic of the AC heating voltage. The detector employs a sensor 100, which may be a resistive metal filament, placed in a cavity 101 through which an effluent from a gas separator flows along with a carrier gas. The metal filament has a resistance which is proportional to the temperature of the filament. The filament may be formed of a refractory metal such as tungsten or platinum.

The sensor 100 is connected to resistors 102, 103, and 104 to form a bridge 108. In the embodiment shown in FIG. 2, the resistor 102 is a dummy sensor which is made, as closely as possible, to be identical to the sensor 100. The dummy sensor 102 is subjected to a flow of pure carrier gas within a cavity 105. By subjecting the dummy sensor 102 to the same ambient environment to which the sensor 100 is subjected, common ambient temperature changes and electronic drift changes are canceled out by the bridge circuit. In other embodiments, the resistor 102 has a fixed resistance.

The resistor 104 is a fixed resistor, while the resistor 103 is a variable resistor to initially balance the bridge.

A signal generator 110 provides power to the bridge 108. The signal generator 110 generates a sinusoidally varying voltage $V_S$ with a frequency f and angular frequency $\omega = 2\pi f$. The frequency f of the signal generator 110 is kept low enough (e.g., 10–40 Hz) so that the temperature of the heated sensor 100 substantially tracks the instantaneous power applied to it.

The preferred temperature of the sensor 100 should be between 5° C. and 100° C. above the walls of the cavity 101. The preferred value of the resistors 100–104 (they should be approximately equal) is 10 to 1000 ohms. The voltage required is given by the relation $$V_S^2/2RGK = \Delta T, \qquad \text{eq. 1}$$

where $\Delta T$ is the temperature rise, $V_S$ is the applied RMS voltage, R is the value of the resistors, G is a geometric factor depending on the dimensions of the sensor whose preferred value is in the range of 0.002 to 0.02 meters, and K is the thermal conductivity of the carrier gas ($\sim 0.15$ at room temperature).

The time dependence of the voltage $V_S$ can be expressed as $$V_S = V_O \cos(\omega t), \qquad \text{eq. 2}$$

where $V_O$ is the peak voltage, $\omega$ is the angular frequency and t is time.

Initially, the bridge 108 is balanced so that the voltage difference between node 112 and node 114 does not have a component which is a third harmonic of $V_S$. A differential amplifier 116 has input terminals connected to the nodes 112 and 114, and an output terminal connected to a measuring circuit 120. The measuring circuit 120 measures the magnitude of the voltage outputted by the amplifier 116 at the third harmonic of the energizing voltage $V_S$.

A reference frequency circuit 121 provides the measuring circuit 120 with a reference signal having a frequency set at an integer multiple of the output frequency of the signal generator 110. This reference frequency is then used by the measuring circuit 120 to effectively filter out all unwanted frequencies except the third harmonic of the energizing voltage $V_S$. The measuring circuit 120 then outputs a voltage corresponding to the magnitude of the third harmonic. The measuring circuit 120 may be a conventional lock-in amplifier, wave analyzer, or sampling voltmeter using a digital filter. If a lock-in amplifier is used, the integer multiple would be three. If a sampling voltmeter is used, the multiple would be the number of samples taken over the period of the fundamental frequency, and would depend on the requirements of the digital filter.

The output signal reflecting the magnitude of this third harmonic is then applied to a recorder 123 or other device to show the magnitude with respect to time of this third harmonic to enable the identification of the various compounds in the effluent.

In operation, if the thermal conductivity of the effluent passing across the sensor 100 changes, the rate of heat loss from the filament of the sensor 100 changes, causing the resistance of the filament to change with respect to the resistance of the dummy sensor 102. The bridge 108 then becomes unbalanced. When the bridge is unbalanced, the change in output voltage $V_A$ is approximately proportional to the product of the energizing voltage $V_S$ and the change in resistance $\Delta R$ of the filament as follows:

$$V_A \alpha V_S \cdot \Delta R. \qquad \text{(eq. 3)}$$

The change in resistance $\Delta R$ is proportional to the change in filament temperature $\Delta T$, so $$V_A \alpha V_S \cdot \Delta T. \qquad \text{(eq. 4)}$$

The change in filament temperature $\Delta T$ is linearly related to the change in heat being removed from the filament. The change in heat being removed from the filament is related to the change in power dissipated by the filament, or $$\Delta \text{ Heat removed } \alpha V_S^2/R. \qquad \text{(eq. 5)}$$

Therefore, combining equations 3, 4, and 5, the change in output voltage $V_A$ due to a change in temperature of the filament in the sensor 100 is related to the voltage $V_S$ outputted from the signal generator 110 as follows:

$$V_A \sim V_S^3/K \text{ or } V_A \sim (V_O \cos \omega t)^3/K, \quad \text{(eq. 6)}$$

where K is a constant related to the thermal conductivity of the effluent flowing across the filament.

Thus, using equivalent trigonometric functions, $V_A$
$$\alpha(\cos\omega t)^3 = (\tfrac{3}{4})\cdot\cos\omega + (\tfrac{1}{4})\cdot\cos 3\omega t. \quad \text{(eq. 7)}$$

In view of equations 2–7, the temperature fluctuation of the sensor 100 due to the flow of effluent passing sensor 100 causes the output voltage $V_A$ of the amplifier 116 to have a Fourier component which is the third harmonic of the voltage $V_S$ outputted by the signal generator 110, and the magnitude of this component is proportional to the change of thermal conductivity of the effluent. Therefore, by measuring the magnitude of this third harmonic, a measure of the presence-and thermal conductivity of a compound eluting from a gas separator may be determined.

The magnitude of this third harmonic is independent of bridge imbalances caused by the drift in the electronics or drift in the resistances of the filaments in the sensor 100 or the dummy sensor 102, since these drifts are unrelated to the frequency of the energizing voltage $V_S$.

To the extent that the sensor 100 and the dummy sensor 102 are matched in resistance and geometry, the third harmonic term will also be insensitive to any variations in the overall bridge 108 temperature, where the bridge structure includes a means for maintaining the walls of the sensor cavities 101 and 105 at as constant a controlled temperature as practical, with a preferred allowed temperature variation of 0.001° C. or less.

The thermal conductivity of a gas varies approximately $10^{-3}$ per Kelvin. A change in thermal conductivity of a gas due to a change in overall bridge 108 temperature is indistinguishable from that due to a change in composition of the gas. Without the compensation provided by the dummy sensor 102, if we wish to detect changes of 10 ppb, we must therefore keep temperature fluctuations of the bridge 108 to less than 10 microKelvin. If the sensor 100 and dummy sensor 102 are matched to 5%, the required temperature control is relaxed by a factor of 20.

Figure 1:
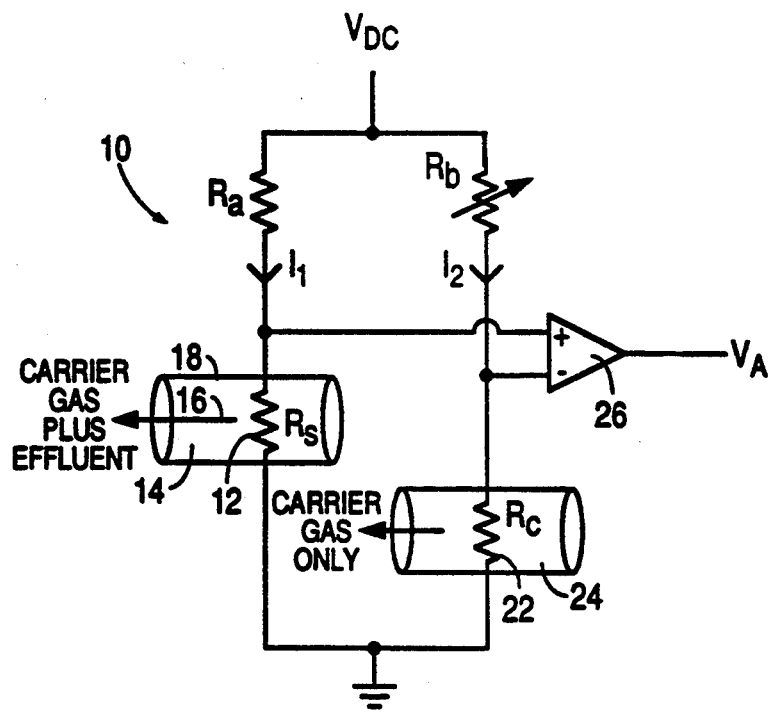
FIG. 1 is a schematic diagram of a prior art thermal conductivity detector.
Figure 3:
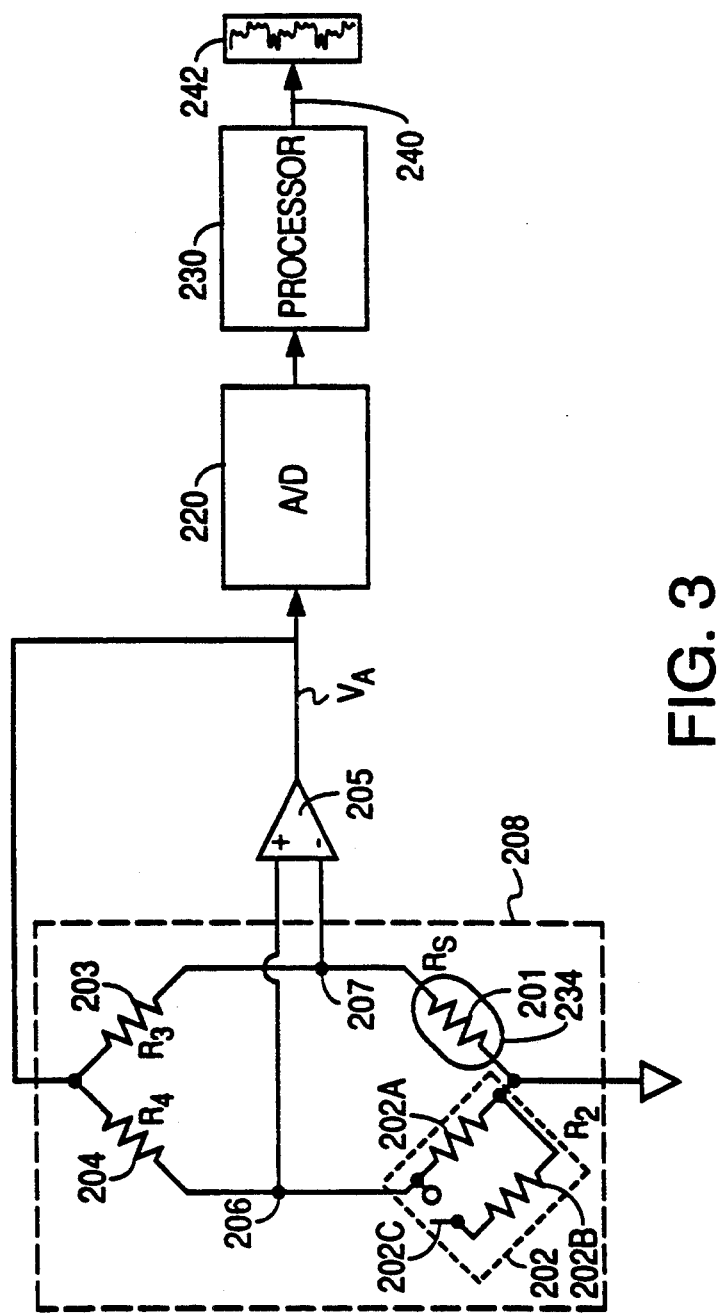
FIG. 3 is a schematic diagram of a thermal conductivity detector which operates at two different temperatures.

FIG. 3 is a schematic diagram of a second embodiment thermal conductivity detector that operates at two different temperatures. The detector includes a sensor 201 which may take the form of the sensor 100 shown in FIG. 1 and described above. A gas whose thermal conductivity is to be measured flows through a cavity 234. The sensor 201 is connected to resistors 202, 203, and 204 in a bridge 208.

The resistor 202 is a variable or switchable resistor which changes its resistance periodically. The resistor 202 includes a controllable switch 202C and fixed resistors 202A and 202B. When the switch 202C is open, the resistor 202 has the resistance of resistor 202A. When the switch 202C is closed, the resistor 202 has the resistance of resistors 202A and 202B connected in parallel. As will be appreciated by those skilled in the art, any type of resistor that is capable of having at least two different resistances may be employed in place of resistor 202.

A differential amplifier 205 has input terminals connected to nodes 206 and 207. The amplifier 205 has an output terminal connected to the common node of resistors 203 and 204 so that the amplifier 205 acts as a variable power supply for dynamically balancing the bridge 208.

The output of the amplifier 205 is also connected to an A/D converter 220, which measures an output voltage $V_A$ of the amplifier 205 and outputs a corresponding digital signal. The A/D converter 220 applies its output signal to a processor 230. The processor 230 calculates the power dissipation changes in the bridge 208 based upon the square of the output voltage $V_A$ at various times. This change in power dissipation is then plotted using a recorder 242 and is used to calculate the thermal conductivity of a sample as described below.

In the embodiment shown in FIG. 3, the resistances $R_2$, $R_3$, and $R_4$ of the resistors 202, 203, and 204, respectively, determine the resistance $R_S$ of the sensor 201 necessary to balance the bridge 208. If $R_3$ and $R_4$ are equal then $R_S$ must equal $R_2$ to balance the bridge.

In operation, the temperature of the sensor 201 is controlled to rise (or fall) by adjusting $V_A$ until the correct resistance $R_S$ is reached to balance the bridge 208. If the resistance $R_2$ is changed, the temperature of the sensor 201 must be changed, by changing $V_A$, to match the new required resistance $R_S$. Therefore, the circuit shown in FIG. 3 effectively changes the required operating temperature of the sensor 201 by switching the resistance of the resistor 202. As noted above, similar changes in operating temperature are accomplished by changing the resistance of resistor 204.

The value of the resistance $R_2$ should be changed about ten to 40 times per second (by switching switch 202C) to ensure any rapid changes in thermal conductivity are measured.

The power P dissipated by the sensor 201 to maintain a certain temperature (and resistance) depends on the thermal conductivity K of the effluent, the temperature difference between the filament and the walls of the cavity 234 ($T_f - T_c$), and the geometry of the sensor 201. Therefore, $$P \alpha K \cdot (T_f - T_c), \quad \text{(eq. 8)}$$

where $T_f$ is the temperature of the filament in the sensor 201 and $T_c$ is the temperature of the walls of the cavity 234.

If the sensor 201 is operated at two different temperatures $T_{f1}$ and $T_{f2}$, two different power dissipations $P_1$ and $P_2$ occur. The difference between the powers are, $$\Delta P = P_1 - P_2 \alpha K \cdot (T_{f1} - T_{f2}), \text{ where} \quad \text{(eq. 9)}$$

this difference is proportional to the thermal conductivity K of the gas and independent of the temperature of the walls of the cavity $T_C$.

The circuit shown in FIG. 3 operates by periodically changing the resistance of the resistor 202 back and forth, using any conventional automatic switching means, between two values and determining the change in power dissipated by a filament in the sensor 201. The voltage $V_A$ needed to balance the bridge 208 is used by the processor 230 to determine the change in power (VI) dissipated by the sensor 201 at the two temperature levels. If the sensor 201 is in thermal equilibrium when the power is determined and the temperature of the container surrounding the filament remains roughly constant between successive determinations, then the change in power dissipation provides a measure of thermal conductivity which is independent of the container temperature. The processor 230 provides the necessary calculations, using $V_A$ and the known resistance values, to output a signal at terminal 240 to a recorder 242 or other device based on the change in power dissipated by the sensor 201 during a cycle. The timing and magnitude of this signal determines the thermal conductivity of the effluent flowing past the sensor 201.

The embodiment of FIG. 3 is only one example of a thermal conductivity detector according to the invention. More generally, any circuit capable of operating a sensor at more than one fixed temperature and capable of measuring power differences may be employed.

Although certain embodiments of the present invention have been described in detail, the description is only an illustration or example of the invention's application and should not be taken as a limitation. The scope of the present invention is defined by the following claims.

I claim:

1. A thermal conductivity detector comprising:
   a sensor having a first terminal connected to a voltage generator for generating an alternating voltage having a frequency, said sensor having a resistance which is dependent on a temperature of said sensor;
   signal providing means, connected to said sensor, for providing a signal which is related to a change in resistance of said sensor; and
   measuring means, connected to said signal providing means, for measuring a magnitude of a component of said signal which has a frequency three times said frequency of said alternating voltage.

2. The thermal conductivity detector of claim 1, wherein said signal providing means comprises:
   a resistive bridge having said sensor connected as one leg of said bridge; and
   a difference amplifier means connected to two nodes of said bridge for outputting a voltage based upon a voltage difference between said two nodes.

3. The thermal conductivity detector of claim 2, wherein said sensor further comprises:
   a resistive element having a resistance that changes in proportion to changes in a temperature of said element, said resistive element being heated by an electric current through said resistive element, said resistive element being contained in a cavity through which a sample fluid flows so that an equilibrium temperature of said resistive element is inversely proportional to a rate of heat transfer between said resistive element and walls of said cavity through said fluid.

4. The thermal conductivity detector of claim 3 wherein said bridge comprises:
   a first impedance having a first and second terminal, said second terminal of said first impedance being connected to a first terminal of said resistive element;
   a second impedance having a first and second terminal, said first terminal of said second impedance being connected to said first terminal of said first impedance;
   a third impedance having a first and second terminal, said first terminal of said third impedance being connected to said second terminal of said second impedance, said second terminal of said third impedance being connected to a second terminal of said resistive element; and
   said voltage generator having first and a second supply voltage terminals, said first supply voltage terminal being connected to said first terminal of said first impedance, said second supply voltage terminal being connected to said second terminal of said resistive element.

5. The thermal conductivity detector of claim 4, wherein said measuring means measures a voltage difference between said first terminal of said resistive element and said first terminal of said third impedance, and determines said magnitude of a component of said voltage difference that varies with a frequency three times said frequency of said voltage generator.

6. The thermal conductivity detector of claim 1 wherein said frequency is between approximately 10 Hz to 40 Hz.

7. A method for determining the thermal conductivity of a sample fluid comprising the steps of:
   applying an alternating voltage to a sensor to vary a temperature of said sensor as a sample gas flows across said sensor, a resistance of said sensor being dependent upon a temperature of said sensor, a frequency of said alternating voltage being sufficiently low such that a temperature of said sensor substantially tracks said alternating voltage;
   measuring an electrical quantity that is related to an instantaneous temperature of said sensor; and
   determining a magnitude of said electrical quantity that has a frequency three times said frequency of said alternating voltage.

8. A method for measuring the thermal conductivity of a sample gas comprising the steps of:
   providing a resistive element in a cavity containing a sample fluid, said resistive element having a resistance which is dependent on a temperature of said resistive element;
   supplying a first amount of power to said resistive element required to cause said resistive element to be at a first predetermined temperature and measuring a quantity corresponding to said first amount of power;
   supplying a second amount of power to said resistive element required to cause said resistive element to be at a second predetermined temperature and measuring a quantity corresponding to said second amount of power; and
   determining a thermal conductivity of said sample fluid based on a difference in said first amount of power and said second amount of power.

9. A thermal conductivity detector comprising:
   a resistive element located in a cavity through which a sample fluid flows, said resistive element having a resistance which is dependent upon a temperature of said resistive element;
   control means, operably connected to said resistive element, for controlling a temperature of said resistive element to be a first predetermined temperature for a first period of time and a second predetermined temperature for a second period of time; and
   measuring means for measuring a quantity related to power dissipated by said resistive element at said first predetermined temperature and said second predetermined temperature.

10. The thermal conductivity detector of claim 9, wherein said means for controlling comprises:
    a resistive bridge having said resistive element connected as one leg of said bridge;
    a variable resistor means connected as another leg of said bridge, said variable resistor means being controllable to switch between a first resistance value, corresponding to said first predetermined temperature of said resistive element, and a second resistance value, corresponding to said second predetermined temperature of said resistive element; and a difference amplifier means connected to two nodes of said bridge for outputting an output voltage based upon a voltage difference between said two nodes, said output voltage being applied to said bridge to heat said resistive element to said first predetermined temperature and said second predetermined temperature.

11. The thernmal conductivity detector of claim 10, further comprising a switching means for periodically controlling said variable resistor means between said first resistance and said second resistance.

12. The thermal conductivity detector of claim 10, further comprising a data processor which detects said output voltage from said difference amplifier and calculates a difference in power being dissipated by said resistive element when said resistive element is at said first predetermined temperature and at said second predetermined temperature, said difference being related to a thermal conductivity of said sample fluid.

13. The method of claim 8 wherein said step of supplying said first amount of power comprises the step of:
balancing a bridge containing said resistive element by providing a current through said resistive element to cause said resistive element to be at said a first predetermined temperature for balancing said bridge, and wherein said step of supplying said second amount of power comprises the step of:
balancing said bridge by supplying a current through said resistive element to cause said resistive element to be at said second predetermined temperature for balancing said bridge.

14. The method of claim 13 wherein said bridge includes a variable resistor means as one leg of said bridge, said variable resistor means being controllable to have a variable resistance value.

* * * * *